United States Patent [19]

Ryan

[11] Plant 4,450

[45] Aug. 14, 1979

[54] IMPATIENS PLANT

[76] Inventor: John J. Ryan, 39877 Sundale Dr., Fremont, Calif. 94538

[21] Appl. No.: 921,996

[22] Filed: Jul. 3, 1978

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Pawnee, and discovered by me in commercial greenhouses in Fremont, Calif. Pawnee is closest in characteristics to patented plant Aztec (U.S. Plant Pat. No. 4,193; a dark yet bright red flower with a white eye) except for color. Its best description would be to call it an orange flowering Aztec with distinctive yellow-green leaf variegation. The outstanding characteristics of Pawnee are its many orange flowers, its distinct yellow-green variegation, its spreading growth habit, and its excellent breaking action, making a good basket plant.

1 Drawing Figure

BACKGROUND OF THE INVENTION

The present new variety (seedling) was discovered by me in a commercial greenhouse in Fremont, Calif., as a result of the cross pollination of the patented pistil parent 76-22-1 (Chickasaw) U.S. Plant Pat. No. 4,260 and the patented pollen parent 76-10-2 (Aztec) U.S. Plant Pat. No. 4,193.

Asexual reproduction of my new cultivar by terminal or stem cuttings grown in pots in a plastic (polyethylene) greenhouse in Fremont, Calif., under normal environmental conditions, show that the characteristics described come true to form and are established and transmitted through succeeding propagations.

Color readings were taken during daylight hours in full sun, and all colors are based on the Royal Horticultural Society Colour Chart.

BRIEF SUMMARY

Pawnee is best described as an orange flowering Aztec with distinct yellow-green leaf variegation. The following are outstanding characteristics of Pawnee:

1. Many orange flowers;
2. A distinctive yellow-green variegated foliage;
3. A spreading growth habit;
4. Excellent breaking action; and
5. Flowers tend to cup more than with Aztec.

DESCRIPTION OF THE PHOTOGRAPH

The accompanying colored photograph illustrates the overall appearance of the cultivar Pawnee, showing a flower color that has more red than usual. Under high light the flower color goes from a red-orange to orange. The inset photograph taken in January 1979, shows the color of the flower as true as reasonably possible for this type of colored reproduction.

DETAILED DESCRIPTION

The following detailed description of Pawnee was based on observations made of the new cultivar on Nov. 3, 1977.

1. PLANT

Name: Pawnee.

Origin: Seedling of the cross pollination of the patented pistil parent 76-22-1 (Chickasaw) U.S. Plant Pat. No. 4,260 and the patented pollen parent 76-10-2 (AZTEC), U.S. Plant Pat. No. 4,193.

Form: Spreading to upright.

Height to flowering: 30 cm.

Growth: Fast.

Type of cutting: Terminal or stem.

Rooting time: Typical, 10 to 14 days.

Rooting habit: Fast, dendritic.

II. FOLIAGE

Arrangement: Lower leaves of any break opposite (usually one set); upper foliage of any break whorls of 3 to 7.

Shape: Lower leaves of break oblanceolate; upper leaves generally elliptic.

Tip: Acuminate.

Base: Attenuate.

Margin: Serrulate.

Veination: Pinnate.

Size: Blade and petiole 6.0 cm. to 9.0 cm.; length of blade 5.0 cm. to 7.5 cm.; width of blade at widest point 1.5 cm. to 3.0 cm.

Surface: Glabrous, semi-glossy.

Variegation: High light and increasing age of leaf increase width and distinctiveness of variegation.

Color:

1. *Petiole.*—50 B.
2. *Veins.*—10 D.
3. *Leaf.*—a. Upper 139 A. b. Lower 138 B to 138 C.
4. *Variegation.*—a. Edge 139 A grades into 6 C. b. Middle 6 C. c. Center 10 D.

III. STEM

Color: 181 A.

Internode:

1. *Length.*—Moderate.
2. *Size.*—Small to moderate.

Node Expanded (relative to internode): Some expansion.

Breaking Action: Very good.

IV: FLOWER

Form: Typical, but slightly cupped.

Borne: End of branches, terminal.

Blooming habit:

2. *Relative number.*—Many.
2. *Time to flowering.*—Short.
3. *Longevity.*—Typical, 3 to 5 days.

Size of mature flower: First flower on a plant may be small.

1. *Length.*—3.5 cm. to 4.0 cm.
2. *Width.*—4.0 cm. to 4.5 cm.
3. *Spur.*—4.5 cm. to 5.5 cm.

Color: Lightens some under high light and heat.

1. *Eye.*—58 B.
2. *Middle.*—40 A.
3. *Edge.*—40 A.
4. *Pedicel.*—47 B grading into 1 D.

V. REPRODUCTIVE ORGANS

Stamen:

| | |
|---|---|
| 1. *Anthers* | Typical, fused hood over pistil |
| 2. *Filaments* | |
| 3. *Pollen.* | |
| a. Color: 158 D. | |
| b. Abundance: Typical, plenty. | |

Pistils:

1. *Style.*—Typical.
2. *Ovaries.*—Typical.

I claim:

1. A new and distinct form of Impatiens plant as described and illustrated, known by the cultivar name Pawnee, and particularly characterized by many orange flowers, a distinctive yellow-green variegated foliage, a spreading growth habit, excellent breaking action, and a slightly cupped flower.

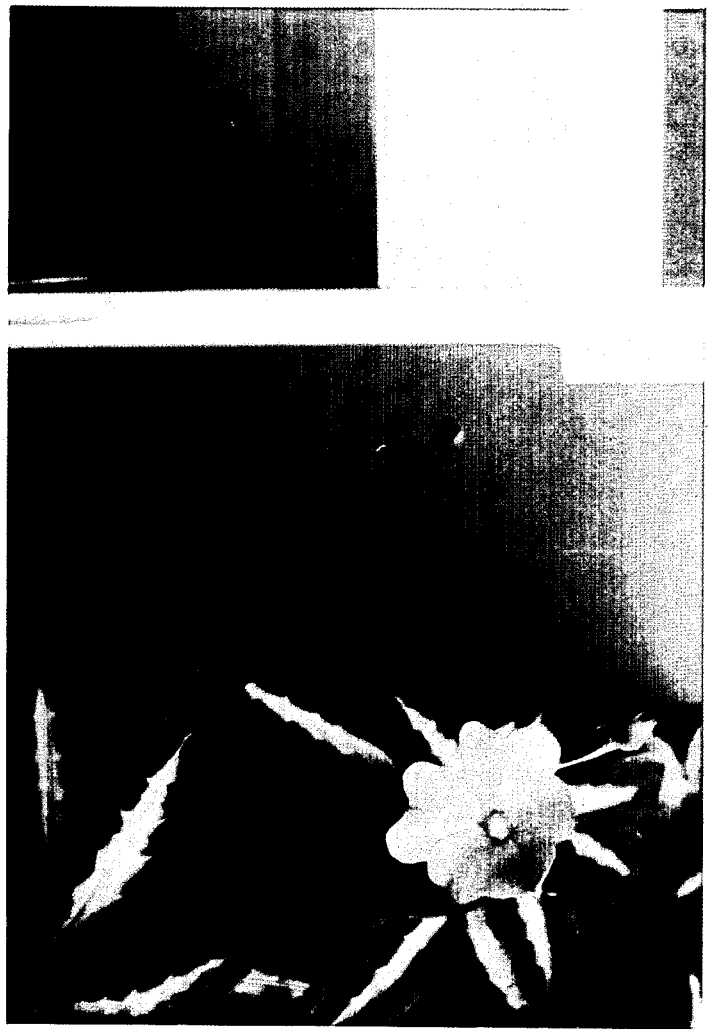

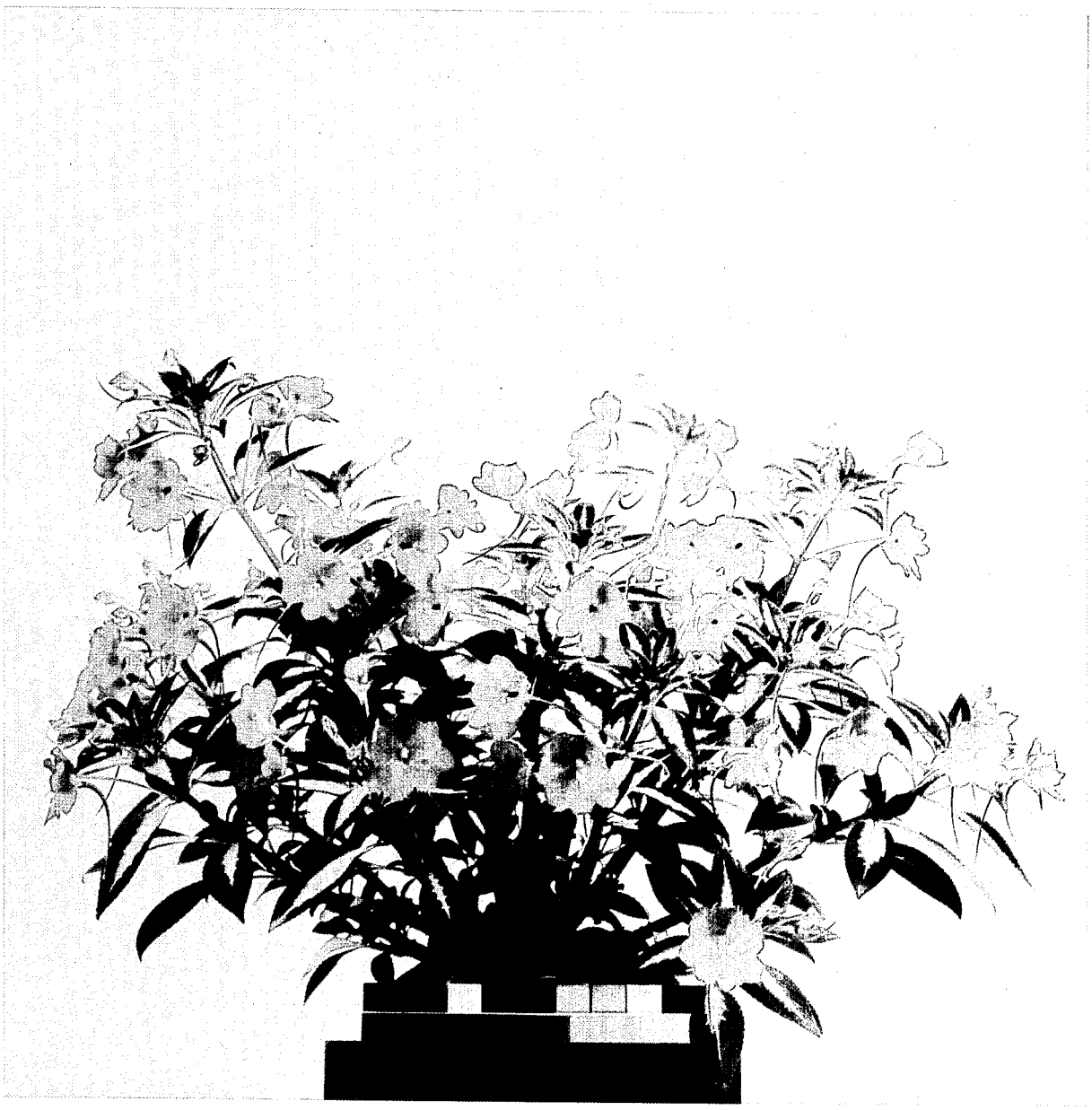

* * * * *